United States Patent
Hancu et al.

(10) Patent No.: US 7,742,800 B2
(45) Date of Patent: Jun. 22, 2010

(54) METHODS AND SYSTEMS FOR DETECTION AND MONITORING OF NEURODEGENERATIVE DISEASES USING MAGNETIC RESONANCE SPECTROSCOPY

(75) Inventors: Ileana Hancu, Clifton Park, NY (US); Napapon Sailasuta, Honolulu, HI (US); Ralph Eugene Hurd, Milpitas, CA (US)

(73) Assignee: General Electric Company, Niskayuna, NY (US)

( * ) Notice: Subject to any disclaimer, the term of this patent is extended or adjusted under 35 U.S.C. 154(b) by 1419 days.

(21) Appl. No.: 11/072,831

(22) Filed: Mar. 4, 2005

(65) Prior Publication Data

US 2005/0251025 A1 Nov. 10, 2005

Related U.S. Application Data

(60) Provisional application No. 60/569,573, filed on May 10, 2004.

(51) Int. Cl.
*A61B 5/05* (2006.01)
(52) U.S. Cl. .................. 600/410; 436/173; 324/307
(58) Field of Classification Search ........... 610/410, 610/409, 422, 431
See application file for complete search history.

(56) References Cited

U.S. PATENT DOCUMENTS

| | | | | |
|---|---|---|---|---|
| 5,617,861 A * | 4/1997 | Ross et al. | .................. | 600/410 |
| 5,657,757 A * | 8/1997 | Hurd et al. | .................. | 600/413 |
| 5,924,987 A * | 7/1999 | Meaney et al. | .................. | 600/420 |
| 6,069,478 A | 5/2000 | Hurd | | |
| 6,104,191 A | 8/2000 | Hurd | | |
| 6,147,492 A * | 11/2000 | Zhang et al. | .................. | 324/309 |
| 2002/0142367 A1 | 10/2002 | Ke et al. | | |
| 2002/0173713 A1 * | 11/2002 | Pfefferbaum et al. | ......... | 600/407 |

OTHER PUBLICATIONS

Lin et al (the effect of Gadolinium on quantitative short echo time single voxel MRS of treated and untreated brain tumors) Proc. Intl. Soc. Mag. Med. 8 (2000).*

Bernd Kuhn, Wolfgang Dreher, Dieter Leibfritz and Martin Heller; "Homonuclear Uncoupled 1H-Spectroscopy of the Human Brain Using Weighted Accumulation Schemes"; Magnetic Resonance Imaging, Tarrytown, NY, US, vol. 17, No. 8, pp. 1193-1201, 1999.

Netherlands Patent Office Search Report, Netherlands Patent Office, Application No. NL 1029000, Mar. 22, 2007.

Kantarci K, Xu Y, Shiung MM, O'Brien PC, Cha RH, Smith GE, Ivnik RJ, Boeve BF, Edland SD, Kokmen E and others. Comparative diagnostic utility of different MR modalities in mild cognitive impairment and Alzheimer's disease. Dement Geriatr Cogn Disord 2002; 14(4):198-207.

(Continued)

*Primary Examiner*—Long V Le
*Assistant Examiner*—Joel F Brutus
(74) *Attorney, Agent, or Firm*—Scott J. Asmus

(57) ABSTRACT

A method for increasing sensitivity and/or specificity of a magnetic resonance spectroscopy imaging technique for detecting a neurodegenerative disease is provided. The method includes acquiring magnetic resonance spectroscopy data from the brain of a subject, while suppressing certain metabolites in the spectrum via a data acquisition protocol, to improve quantification accuracy for the remaining metabolites, and quantifying a metabolite concentration or a metabolite concentration ratio from the spectral data as an indicator of the neurodegenerative disease.

23 Claims, 5 Drawing Sheets

OTHER PUBLICATIONS

Krishnan KRR, Charles CC, Doraiswamy PM, Mintzer J, Weisler R, Yu X, Perdomo C, Ieni JR, Rogers S. Randomized, placebo-controlled trial of the effects of Donepezil on neuronal markers and hippocampal volumes in Alzheimer's disease. Am J Psychiatry 2003; 160:2003-2011.

* cited by examiner

METHODS AND SYSTEMS FOR DETECTION AND MONITORING OF NEURODEGENERATIVE DISEASES USING MAGNETIC RESONANCE SPECTROSCOPY

CROSS REFERENCE TO RELATED APPLICATIONS

This application is a non-provisional application of the provisional application Ser. No. 60/569,573, filed May 10, 2004, which is herein incorporated by reference.

BACKGROUND

The invention relates generally to a magnetic resonance spectroscopy (MRS) data acquisition technique and in particular to detection and monitoring of a neurodegenerative disease using this MRS technique.

The use of nuclear magnetic resonance spectroscopy data acquisition techniques for the determination of the presence and/or concentrations of individual chemical compounds is known as MR spectroscopy (MRS). Magnetic resonance spectroscopy is generally considered as a possible sensitive, non-invasive technique for detecting neurodegenerative diseases and monitoring therapy in such diseases. However, repeatability issues associated with the common spectroscopy techniques, as well as the inherent biological variability make the sensitivity/specificity of these techniques less than ideal in tracking metabolite changes due to disease or treatment.

Common spectroscopy techniques employed for neurodegenerative diseases detection and treatment monitoring generally include data acquisition protocols like STEAM (stimulated echo acquisition mode) and PRESS (Point RESolved Spectroscopy, a double spin echo imaging sequence). The spectra yielded by these two sequences are extremely complex, as all of the protons in the selected region of brain tissue produce a detectable signal. Consequently, it is difficult to reliably extract the concentration of every metabolite in the brain, and in particular the concentration of metabolites that change with disease and treatment. Therefore, relatively low sensitivity and specificity exist for MRS techniques in detecting early stages of a neurodegenerative disease such as Alzheimer disease (AD). AD is a progressive neurodegenerative disease, and even though its symptoms were first described almost a century ago, no definitive diagnostic exists even now. A "probable AD" diagnostic is usually given based on a series of neuropsychological, imaging and laboratory tests, only to ultimately be confirmed or infirmed (in ~10% of the cases) through post-mortem pathological examinations. For example using existing MRS techniques, a patient may be classified as "probable" AD, that is, with a sensitivity (true positive rate) and specificity (false positive rate) for less than ideal (ideal numbers being 100% and 0%). Moreover, clinical studies that have used MRS as a marker for treatment efficacy involve a large number of subjects (treated and untreated) in order to show a statistically significant difference that could be assigned to the treatment.

Therefore there is a need for using more sensitive imaging or MRS techniques for detecting the metabolites of interest for early detection and treatment of a neurodegenerative disease in a patient. There is also a need to identify a suitable neuronal integrity marker that could be used as an indicator for the existence of the disease and follow its response to therapy in a timely fashion.

BRIEF DESCRIPTION

Briefly, in accordance with one aspect of the present technique, a method for increasing sensitivity and/or specificity of a magnetic resonance spectroscopy technique to diagnose or monitor a disease is provided. The method includes acquiring magnetic resonance spectroscopy data from the brain of a subject, suppressing some of the overlapping metabolite signals in the spectral data via a data acquisition protocol, and quantifying the remaining metabolite concentrations or metabolite concentration ratios from the spectral data as an indicator of a neurodegenerative disease.

In accordance with another aspect, an MR spectroscopy system is provided. The system includes a set of gradient coils for producing controlled gradient field, a radio frequency coil for applying excitation signals to a subject of interest, and a detecting coil for detecting magnetic resonance signals resulting from the excitation signals. The system also includes a control and acquisition circuitry configured to energize the set of gradient coils and to acquire magnetic resonance spectroscopy data, wherein certain overlapping metabolite signals are suppressed in the spectral data via a data acquisition protocol. A post processing component may also be provided to quantify metabolite concentrations or metabolite concentration ratios for at least N-acetyl aspartate and N-acetyl aspartate/Creatine from the spectral data as an indicator of a neurodegenerative disease.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Aspects of the present technique include methods and systems for sensitive detection and monitoring of brain metabolite concentrations or changes in metabolite concentrations due to neurodegenerative diseases or due to treatment of such diseases. The metabolite concentration referred to herein means the chemical levels of the cellularly partitioned metabolites in the brain.

Figure 1:
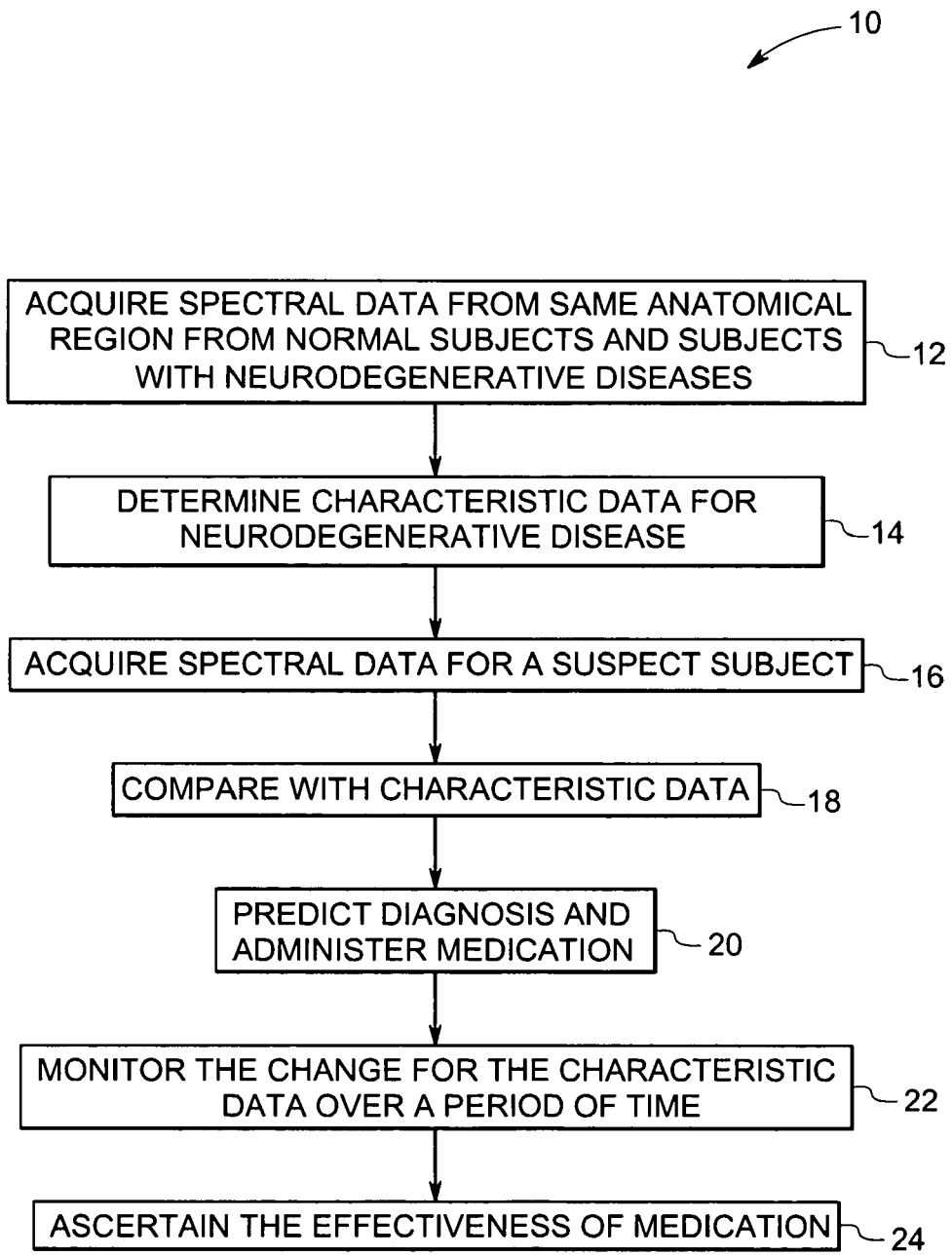
FIG. 1 is a flowchart illustrating exemplary steps for a method for detecting and monitoring a neurodegenerative disease according to aspects of the present technique.

FIG. 1 is a flowchart 10 showing exemplary steps for detecting a neurodegenerative disease according to aspects of the present technique. The method includes acquiring spectral data at step 12. For diagnosis, the technique will be performed on a single patient and for clinical trials (for example, trial of a new pharmaceutical agent), the spectral data is typically the magnetic resonance spectroscopy (MRS) data from an anatomical region of clinically diagnosed subjects with neurodegenerative diseases (disease group) and from the same anatomical region of subjects that are normal and aged-matched controls (normal control group) for the disease group. Regions of brain (for example, hippocampus, posterior cingulate gyrus) are typically used as the anatomical regions for detecting the neurodegenerative diseases. Certain neurodegenerative diseases exhibit specific changes in the chemical composition of brain tissues as disease state advances or responds to a treatment. For example, there are consistent changes in certain neuronal integrity markers that are associated with Alzheimer disease (AD), these are increases in myoInositol (mI) and its ratio to creatine (Cr), as well as decreases in N-acetyl aspartate (NAA), NAA/Cr and NAA/mI. NAA is the metabolite reflecting neuronal integrity with the highest concentration in the brain, and its spectrum is much simpler than the one of mI, due to the presence of the protons in the acetyl moiety at 2.01 ppm. Changes in NAA have been reported as a consequence of AD treatment.

An embodiment of the present technique makes use of an MRS technique called as echo time (TE) averaged Point RESolved Spectroscopy (PRESS-J), that offers an attractive means to reliably quantify glutamate (Glu) at 3 Tesla (3 T). The present technique makes use of the fact that PRESS-J effectively cancels magnetization from the outer wings of multiplets, leaving only signal coincident in frequency with chemical shift. Therefore, the present technique advantageously uses PRESS-J to suppress Glutamate and Glutamine wings from around 2 ppm in the spectral data, allowing more accurate quantification of N-acetyl aspartate. An aspect of the present technique includes assessing different data acquisition protocols for their appropriateness in detecting the neurodegenerative diseases and the same is explained in more detail with reference to FIG. 3 and FIG. 4.

At step 14 in FIG. 1 the spectral data from the disease group and from the normal control group is compared. The exemplary steps to compare the spectral data are explained in more detail with reference to FIG. 2. In one example, using aspects of the present technique, significant differences were observed in the data acquired from subjects with neurodegenerative diseases as compared with data from normal, age-matched controls. On the basis of the compared spectral data between the disease group and the normal control group, a characteristic data for example, a representative metabolite concentration is selected as an indicator of a specific neurodegenerative disease and also an indicator of the stage of the disease.

Figure 2:
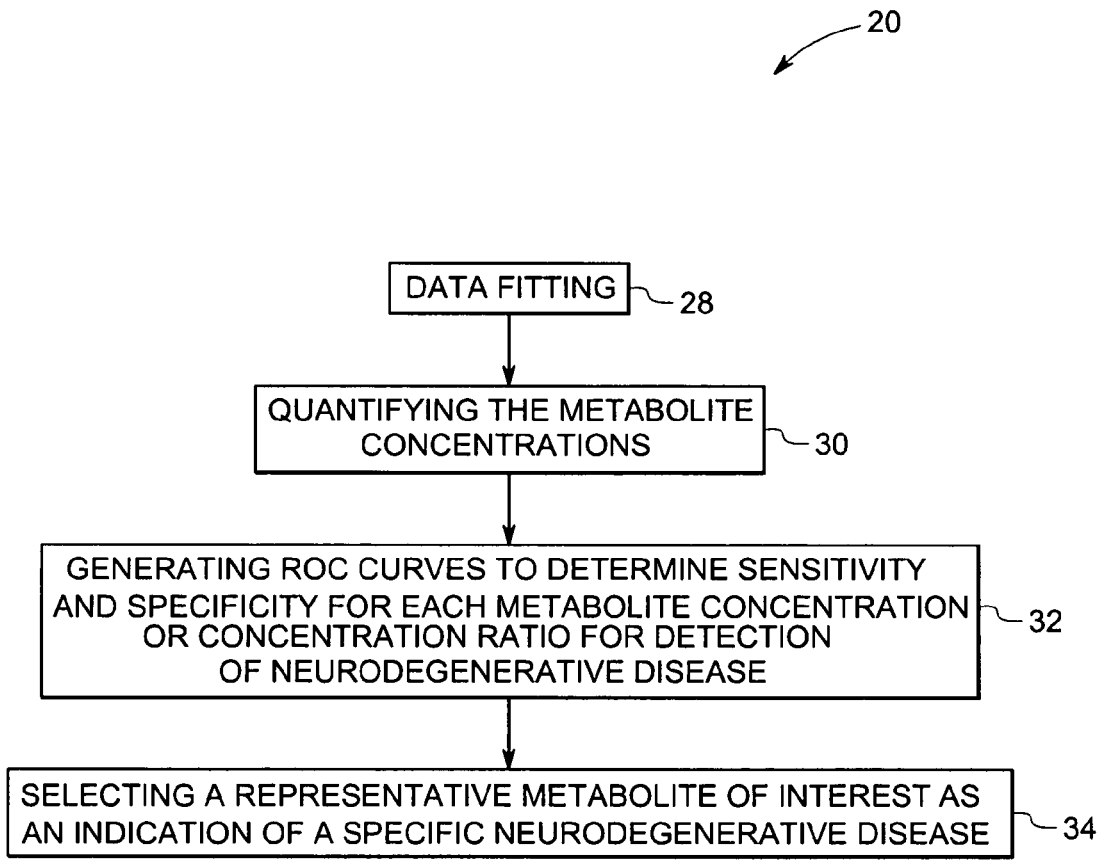
FIG. 2 is a flowchart showing exemplary steps for comparing data for a disease group and for a normal control group, and for deriving characteristic data representative of the neurodegenerative disease.

Subsequently, additional patients suspected of having the neurodegenerative disease (e.g. probable Alzheimer disease) may be selected. It may be well appreciated by those skilled in the art that steps 12 and 14 as described above, may only need to be performed once to obtain characteristic data. At step 16, spectral data may be acquired for a suspect subject (suspected as a neurodegenerative disease patient). The spectral data may be acquired using the same PRESS-J sequence. In a present implementation, the data quantification techniques as explained in FIG. 2 are used and at step 18 the spectral data from the suspect subject is compared with the characteristic data. At step 20 diagnosis is made on the basis of the comparison with the characteristic data (metabolite concentration of the representative metabolite of interest).

Aspects of the present technique include monitoring the spectral data in case a neurodegenerative disease is detected, as indicated in step 22. In case a person is undergoing treatment, aspects of the present technique may be used to determine the efficacy of the treatment, for example, the effect on the disease due to a particular drug or any other alternate therapy administered to the patient, as illustrated in step 24. Thus, the evolution of the disease i.e. either progression or control may also be effectively analyzed using aspects of the present technique. In one example, in order to assess impact of a drug on brain neurochemistry, a pool of patients suspected of a neurodegenerative disease treated with a particular medication may be selected, as well as a similar, but untreated pool. Spectral data may be acquired using PRESS-J from the same regions in the brain. Following data quantification, metabolite and metabolite ratios may be pooled together for treated and untreated groups, and evidence may be sought for differences in the average values of metabolite concentrations and concentration ratios for treated and untreated groups, and thus to assess the effect of the drug on brain neurochemistry. Due to the sensitivity and specificity of the present technique smaller participant groups are needed for such a determination.

FIG. 2 is a flowchart 26 showing exemplary steps for comparing the data for the disease group and for the normal control group, and for deriving the characteristic data representative of a neurodegenerative disease (step 14 of FIG. 1). At step 28, appropriate data fitting technique may be used, for example frequency domain fitting or time domain fitting. At step 30 data may be quantified and metabolite concentration for metabolites of interest may be measured. In one example, significant decreases in the n-acetyl-aspartate (NAA) and n-acetyl-aspartate/creatine (Cr) ratios for early Alzheimer disease patients were observed as compared to normal, age-matched controls. At step 32 receiver operating characteristic (ROC) curves may be generated for the metabolites (or metaobolite ratios) of interest by using peak area, peak heights or fitted metabolite concentrations or concentration ratios as the determining attributes. ROC curves depict sensitivity versus specificity of the technique in detecting a particular neurodegenerative disease. A particular sensitivity/specificity in detecting the disease may be chosen (e.g., 80% sensitivity=true positive rate, 20% specificity=false positive rate). At step 34 the value or values of metabolite concentration or metabolite concentration ratio (metabolite ratio) having the highest specificity at a given sensitivity rate in detecting the disease are noted and the corresponding metabolite (or the corresponding metabolite concentration or a metabolite ratio) is selected as a representative metabolite for detecting a specific neurodegenerative disease.

It will be well understood by those skilled in the art that steps 28-32 may also be employed for quantifying the data for suspect patients, according to aspects of the present technique. By comparing the values of different metabolites and metabolite ratios from the suspect patients with the ones established to correspond to the threshold of separation between normal and neurodegenerative state at the level of sensitivity/specificity chosen, considering certain characteristic data, a diagnosis (either positive or negative) may be made for the subjects having the possibility to have the neurodegenerative disease or not. In a present implementation described below, the characteristic data includes NAA concentration and NAA/Cr (Creatine) ratio as an indicator of AD.

Figure 3:
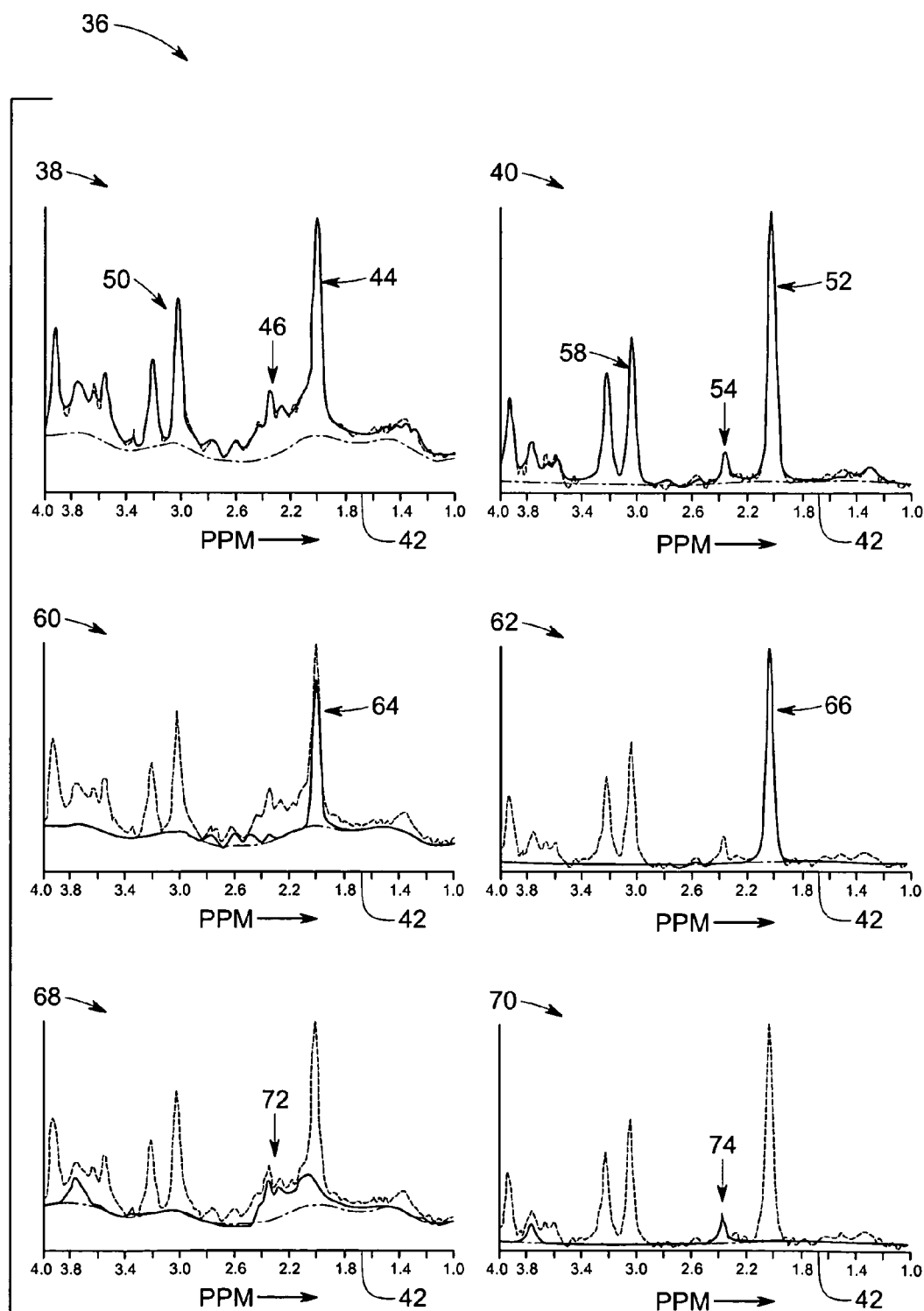
FIG. 3 is graphical representation of the components of the fitted spectral lines for two MRS data acquisition techniques PRESS and PRESS-J.

FIG. 3 is a graphical illustration of the components of the fitted spectral lines for different metabolites of interest as obtained according to one aspect of the present technique using two exemplary data acquisition protocols, PRESS and PRESS-J. The graphical representation contains spectral peaks from metabolites of interest. Graphical profiles 38 and 40 illustrate a composite expression of spectral data displayed between 1.0 to 4.0 ppm (parts per million) as illustrated by reference numeral 42, from the brain of a normal subject using PRESS and PRESS-J, respectively. Peaks or regions 44, 46, 50 correspond to metabolite concentrations for NAA, the overlap of Glu (Glutamate) and Gln (Glutamine) and Cr (Creatine), respectively determined using the PRESS protocol. Peaks or regions 52, 54, and 58 correspond similarly to NAA, Glu, and Cr, respectively, determined using the PRESS-J protocol. Using this protocol, the Gln peak is completely suppressed. After doing appropriate data fitting on both these profiles 38 and 40, different components of the metabolites present in vivo can be extracted, such as 60 and 62, and 68 and 70.

Graphical profiles 60 and 62 represent the contribution of N-acetyl aspartate (NAA) to the overall fit in the PRESS and PRESS-J spectrum, respectively. Graphical profile 60 depicts the fitted spectral line for NAA, whose main spectral peak is denoted by reference numeral 64 and obtained from the spectral data acquired using the PRESS protocol. Similarly, graphical profile 62 depicts the fitted spectral line for NAA, whose main spectral peak is denoted by reference numeral 66 and obtained from the spectral data acquired using the PRESS-J protocol. It is clear from the graphical profiles 60 and 62 that PRESS-J provided a clearer and more sensitive representation for NAA over PRESS spectral data. The Glu and other peaks under NAA are better suppressed using PRESS-J, leading to better quantification for NAA. Graphical profiles 68 and 70 denote the fitted spectral lines for Glu acquired using PRESS and PRESS-J respectively. Regions 72 and 74 denote peaks for Glu from the PRESS and PRESS-J spectral data, respectively. It appears that PRESS-J data for Glu may be more sensitive over PRESS for measuring the concentration of this specific metabolite. In general, it was observed that PRESS-J simplifies the spectral lines, while keeping the singlets in the spectrum, and thus is more sensitive for measuring metabolite concentrations whose spectra include these singlets.

Figure 4:
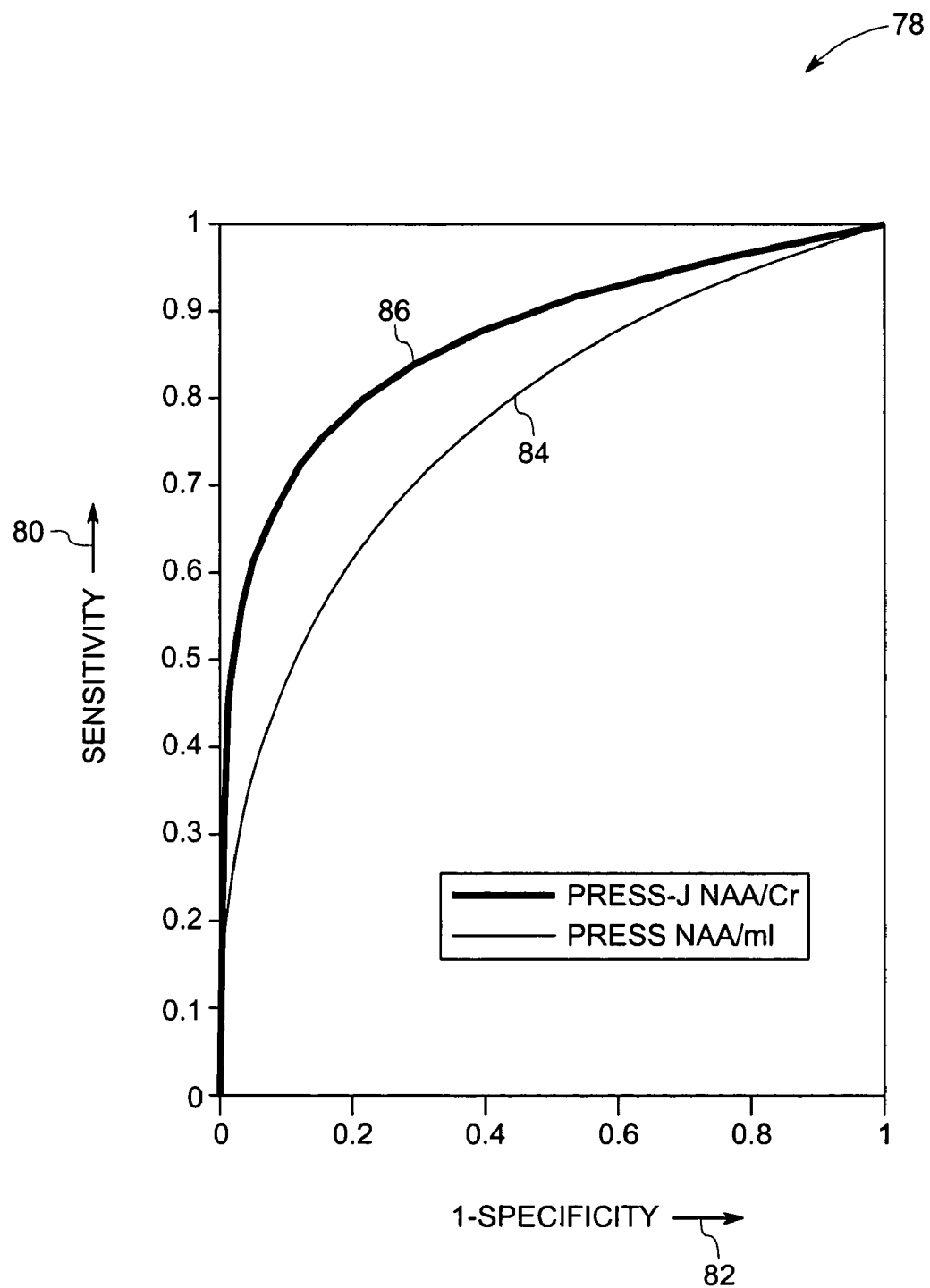
FIG. 4 is a graphical representation of binormal receiver operating characteristic (ROC) curves for certain metabolite ratios, for showing the sensitivity and specificity for PRESS and PRESS-J data acquisition techniques.

FIG. 4 is a graphical representation, designated generally by reference numeral 78, of the conventional binormal ROC curves, 84 and 86 obtained from the NAA/mI metabolite ratios obtained from PRESS, and from NAA/Cr ratio obtained with PRESS-J acquisition protocols, respectively. The ROC curves were obtained by studying a group of 20 subjects diagnosed with probable Alzheimer's disease, and 20 age-matched normal volunteers. These discriminant functions (characteristic data, i.e. NAA/mI and NAA/Cr ratios) are derived from discriminant function analysis for both pulse sequences. These functions are composed of a single predictor, the N-acetyl aspartate (NAA)/Creatine (Cr) ratio for PRESS-J, and the NAA/myoInositol (mI) ratio for PRESS. ROC curves are a measure of sensitivity denoted by axis designated by reference numeral 80 and specificity denoted by axis 82. The area under the curves is an indicator of how sensitive a method is in identifying patients affected by a disease. As is shown in FIG. 4, the area under the curve 86 is more than the area under the 84, indicating that higher sensitivity was observed at all specificities for PRESS-J.

Table 1 presents experimental results depicting the average intra-day, intra-individual coefficients of variation (CV) for all the metabolite concentration and concentration ratios fitted from the spectra of two normal volunteers, scanned repeatedly on multiple daily sessions during the course of six months. Along with the actual coefficients of variation, the Cramer Rao lower bounds (CRLB's) reported by LCModel are presented in the table, in good qualitative agreement with the CV's. LCModel is a commonly available data quantification program, described in Provencher SW. Estimation of metabolite concentrations from localized in vivo proton NMR spectra, and the CRLB's are a good measure of how precise the measurement of a metabolite concentration is; the lower the CRLB's, the higher the precision. As can be noticed, the singlets Cr, Cho (Choline), Cho/Cr, NAA, NAA/Cr have consistently lower CV's and CRLB's when data is acquired using PRESS-J.

TABLE 1

|  | Cr | Glu | Glu/Cr | mI | mI/Cr | Cho | Cho/Cr | NAA | NAA/Cr | NAA/mI |
| --- | --- | --- | --- | --- | --- | --- | --- | --- | --- | --- |
| CV PRESS [%] | 4.74 | 6.50 | 7.34 | 7.51 | 6.27 | 5.67 | 5.69 | 4.47 | 4.79 | 7.38 |
| CRLB PRESS | 3.94 | 7.76 |  | 8.27 |  | 5.88 |  | 3.97 |  |  |
| CV PRESS-J [%] | 3.56 | 7.59 | 8.30 | 13.57 | 12.92 | 3.25 | 3.40 | 2.74 | 2.57 | 13.64 |
| CRLB PRESS-J | 3.55 | 10.36 |  | 14.06 |  | 4.15 |  | 2.18 |  |  |

Thus, it is clear from the experimental results as tabulated above that PRESS-J offers more reproducible measurements of metabolite concentrations and concentration ratios of singlets, like NAA, NAA/Cr, Cho and Cr.

Figure 5:
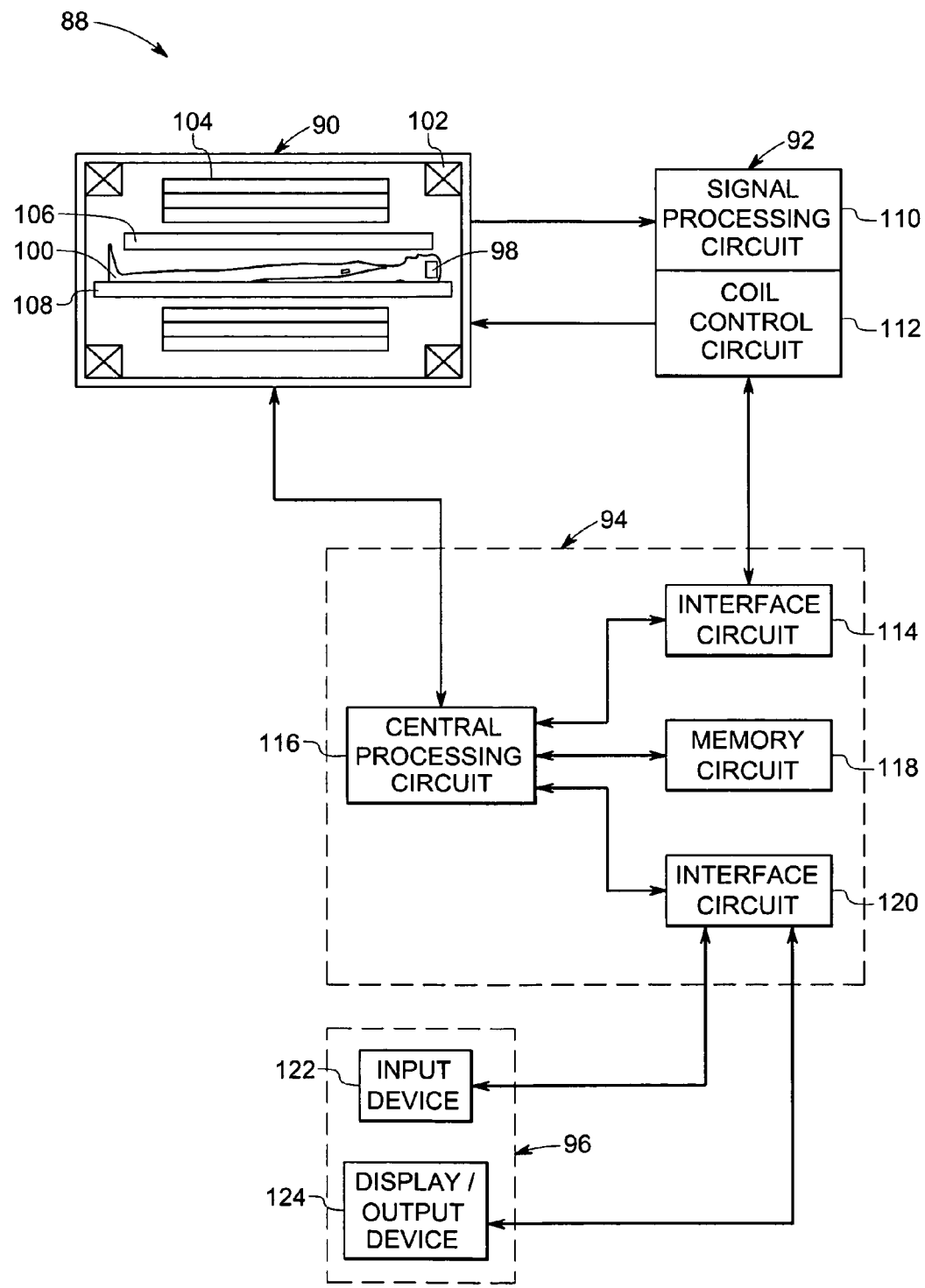
FIG. 5 is a diagrammatical representation of an exemplary magnetic resonance spectroscopy (MRS) system in accordance with aspects of the present technique.

Referring now to FIG. 5, an exemplary magnetic resonance spectroscopy system, designated generally by the reference numeral 88, is illustrated for use in the present technique. The system includes a magnet assembly 90, a control and acquisition circuit 92, a system controller circuit 94, and an operator interface station 96. The magnet assembly 88, in turn, includes coil assemblies for selectively generating controlled magnetic fields used to excite gyromagnetic materials spin systems in a region of interest 98 in a subject 100. In particular, the magnet assembly 88 includes a primary coil 102, which will typically include a superconducting magnet coupled to a cryogenic refrigeration system (not shown). The primary coil 102 generates a highly uniform B0 magnetic field along a longitudinal axis of the magnet assembly. A gradient coil assembly 104 consisting of a series of gradient coils is also provided for generating controllable gradient magnetic fields having desired orientations with respect to the anatomy or region of interest 98. In particular, as will be appreciated by those skilled in the art, the gradient coil assembly produces fields in response to pulsed signals for selecting an image slice, orienting the image slice, and encoding excited gyromagnetic material spin systems within the slice to produce the desired image. In spectroscopy systems these gradient fields may be used differently. An RF transmit/receive coil 106 is provided for generating excitation signals that result in MR emissions from the subject 100 that are influenced by the gradient fields, and collected for analysis as described below. In the receive mode, the coils 106 receive the MR signals generated from the anatomy of interest 98 and the signals are collected for analysis as described below.

A table 108 is positioned within the magnet assembly 90 to support the subject 100. While a full body MRS system is illustrated in the exemplary embodiment of FIG. 5, the technique described below may be equally well applied to various alternative configurations of systems and scanners, including smaller scanners and probes used in MR applications, particularly for analyzing neural tissue of the brain.

In the embodiment illustrated in FIG. 5, the control and acquisition circuit 92 includes a signal processing circuit 110 and a coil control circuit 112. The coil control circuit 112 receives pulse sequence descriptions from the system controller 94, notably through an interface circuit 114 included in the system controller 94. As will be appreciated by those skilled in the art, such pulse sequence descriptions generally include digitized data defining pulses for exciting the coils of the gradient coil assembly 104 during excitation and data acquisition phases of operation.

Fields generated by the transmit coil assembly 106 excite the spin system within the subject 100 to cause emissions from the anatomy of interest 98. Such emissions are detected by coils 106 and are filtered, amplified, and transmitted to signal processing circuit 110. Signal processing circuit 110 may perform preliminary processing of the detected signals, such as amplification of the signals. Following such processing, the amplified signals are transmitted to the interface circuit 114 for further processing.

In addition to the interface circuit 114, the system controller 94 includes central processing circuit 116, memory circuit 118, and interface circuit 120 for communicating with the operator interface station 96. In general, the central processing circuit 116, which will typically include a digital signal processor, a CPU or the like, as well as associated signal processing circuit, commands excitation and data acquisition pulse sequences for the magnet assembly 90 and the control and acquisition circuit 92 through the intermediary of the interface circuit 114. The central processing circuit 116 also processes image data received via the interface circuit 114, to perform fast Fourier transforms to convert the acquired data from the time domain to the frequency domain, and to reconstruct the data into a meaningful image. The central processing circuit may also be configured for quantifying metabolite concentration/ratios for metabolites of interest (for example NAA) from the spectral data as an indicator of a neurodegenerative disease; and for monitoring a change in the metabolite concentration for NAA over a period of time through the treatment process as an indicator of progression or digression of the neurodegenerative disease. The imaging system may have a post processing component in the central processing unit to perform the quantification and/or monitoring function or the post processing component may be a part of an external device situated at a remote location, for example at the doctor's clinic. The memory circuit 118 serves to save such data, as well as pulse sequence descriptions, configuration parameters, and so forth. The interface circuit 120 permits the system controller 94 to receive and transmit configuration parameters, image protocol and command instructions, and so forth.

The operator interface station 96 includes one or more input devices 122, along with one or more display or output devices 124. In a typical application, the input device 122 will include a conventional operator keyboard, or other operator input devices for selecting image types, image slice orientations, configuration parameters, and so forth, and for controlling the examination. The display/output device 124 will typically include a computer monitor for displaying the operator selections, as well as for viewing scanned and reconstructed images. Such devices may also include printers or other peripherals for reproducing hard copies of the reconstructed images.

Various aspects of the present techniques are advantageous as they result in sensitive detection of changes in metabolite concentrations or metabolite concentration ratios (in particular NAA, NAA/Cr) due to neurodegenerative diseases or treatment of such diseases. The techniques may be used for diagnosis of neurodegenerative diseases (e.g. AD) in particular, as well for assessing response to the treatment of these diseases. These techniques are advantageously more sensitive for detecting changes associated with early disease than the currently employed MRS techniques. Also, aspects of the present technique require a smaller group size for any clinical drug trail, significantly decreasing their cost.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for increasing sensitivity and/or specificity of a magnetic resonance spectroscopy imaging technique in detecting a neurodegenerative disease, the method comprising:

acquiring magnetic resonance spectroscopy data from the brain of a subject, by using a data acquisition technique that suppresses resonances in a spectrum, while keeping spectral peaks from metabolites of interest in the spectrum, wherein the data acquisition technique is PRESS-J;

quantifying a concentration or concentration ratios of a plurality of metabolites present in the spectrum; and using the concentration or concentration ratios of the metabolites of interest as an indicator of a neurodegenerative disease.

2. The method of claim 1, further comprising identifying early stages of a neurodegenerative disease.

3. The method of claim 1, further comprising comparing the concentration or concentration ratios of the metabolites of interest for healthy volunteers and patients diagnosed with neurodegenerative diseases.

4. The method of claim 1, wherein the resonances in the spectrum that are suppressed belong to Glutamate and Glutamine.

5. The method of claim 1, further comprising aiding monitoring a disease or treatment of the disease for a patient diagnosed with the neurodegenerative disease by detecting change over time in the metabolite concentration or metabolite ratios of at least N-acetyl aspartate and/or and N-acetyl aspartate/Creatine.

6. The method of claim 1, wherein the neurodegenerative disease is Alzheimer disease.

7. A method for increasing sensitivity/specificity of a magnetic resonance spectroscopy imaging technique, the method comprising:
  acquiring magnetic resonance spectroscopy data from the brain of a subject via PRESS-J data acquisition protocol;
  quantifying the concentrations or concentration ratios for metabolites of interest from the spectral data; and
  selecting a representative metabolite of interest or a representative ratio of the metabolites of interest as an indicator of a neurodegenerative disease.

8. The method of claim 7, further comprising detecting the neurodegenerative disease on the basis of the representative metabolite of interest.

9. The method of claim 8, wherein the representative metabolite of interest is N-acetyl aspartate.

10. The method of claim 7, wherein the representative ratio of metabolites of interest is N-acetyl aspartate/Creatine.

11. The method of claim 7, further comprising monitoring a change in the representative metabolite of interest or the representative ratio of metabolites of interest over time as an indicator of evolution of the neurodegenerative disease.

12. A method for aiding a clinical trial for treatment of a neurodegenerative disease, the method comprising:
  acquiring magnetic resonance spectroscopy data of the brain of a subject by using a data acquisition technique that suppresses resonances in a spectrum to improve quantification accuracy for metabolites of interest in the spectrum, wherein the data acquisition technique is PRESS-J;
  quantifying metabolite concentrations or metabolite concentration ratios for at least N-acetyl aspartate and/or and N-acetyl aspartate/Creatine from the spectral data as an indicator of a neurodegenerative disease;
  administering a pharmaceutical agent to the subject; and
  monitoring a change in the metabolite concentration or metabolite concentration ratio for N-acetyl aspartate and/or and N-acetyl aspartate/Creatine over time to test the effectiveness of the pharmaceutical agent.

13. The method of claim 12, wherein the neurodegenerative disease is Alzheimer disease.

14. A method for analyzing evolution of a neurodegenerative disease in a subject, the method comprising:
  acquiring magnetic resonance spectroscopy data of the brain of a subject, by using a data acquisition technique, wherein the data acquisition technique is PRESS-J, wherein magnetic resonance spectroscopy data for one or more of N-acetyl aspartate or N-acetyl aspartate/Creatine have intra-day, intra-individual coefficients of variation, respectively, of less than or equal to 2.74 or 2.57;
  quantifying a metabolite concentration or metabolite concentration ratio for at least N-acetyl aspartate and/or and N-acetyl aspartate/Creatine from the spectral data as an indicator of a neurodegenerative disease; and
  monitoring a change in the metabolite concentration or the metabolite concentration ratio for N-acetyl aspartate and/or and N-acetyl aspartate/Creatine over time as an indicator of evolution of the neurodegenerative disease.

15. The method of claim 14, wherein the neurodegenerative disease is Alzheimer disease.

16. A method for aiding a diagnosis of a neurodegenerative disease in a subject, the method comprising:
  acquiring magnetic resonance spectroscopy data from brain tissues of the subject, by using a data acquisition technique that suppresses resonances in a spectrum, to improve quantification accuracy for metabolites of interest, wherein the data acquisition technique is PRESS-J;
  quantifying a metabolite concentration or a metabolite concentration ratio for at least N-acetyl aspartate and/or and N-acetyl aspartate/Creatine from the spectral data as an indicator of a neurodegenerative disease; and
  comparing the metabolite concentration or the metabolite concentration ratio for N-acetyl aspartate and/or and N-acetyl aspartate/Creatine with a threshold value for N-acetyl aspartate and/or and N-acetyl aspartate/Creatine used for separation between a normal and a neurodegenerative state.

17. A method for increasing sensitivity or specificity of a magnetic resonance spectroscopy imaging technique, the method comprising:
  acquiring magnetic resonance spectroscopy data from brain tissues of a subject, by using a data acquisition technique that suppresses resonances in a spectrum, to improve quantification accuracy for metabolites of interest, wherein the data acquisition technique is PRESS-J;
  quantifying a metabolite concentration or a metabolite concentration ratio for metabolites of interest from the spectral data;
  comparing the sensitivity and specificity for each metabolite concentration or concentration ratio of interest for detecting a neurodegenerative disease; and
  selecting one or more representative metabolite of interest as an indicator of the neurodegenerative disease.

18. The method of claim 17, further comprising detecting the neurodegenerative disease in the subject based on the metabolite concentration or metabolite concentration ratio of the one or more representative metabolite of interest.

19. The method of claim 17, further comprising monitoring a change over time in the metabolite concentration or the metabolite concentration ratio for the metabolite of interest in the subject with the neurodegenerative disease.

20. The method of claim 17, wherein the metabolite of interest is N-acetyl aspartate.

21. An MR spectroscopy system comprising:
  a set of gradient coils for producing controlled gradient field;
  a radio frequency coil for applying excitation signals to a subject of interest;
  a detecting coil for detecting magnetic resonance signals resulting from the excitation signals;
  a control and acquisition circuitry configured to energize the set of gradient coils and RF coils and to acquire magnetic resonance spectroscopy data, wherein resonances are suppressed in the spectral data via a data acquisition protocol, to improve data quantification accuracy for metabolites of interest, wherein the data acquisition protocol is PRESS-J;
  a system controller circuit configured to obtain an image having metabolite distinction from the acquired magnetic resonance spectroscopy data; and
  a post processing component configured for quantifying a metabolite concentration or a metabolite concentration ratio for at least N-acetyl aspartate and/or and N-acetyl aspartate/Creatine from the spectral data as an indicator of a neurodegenerative disease.

22. A memory circuit for storing computer instructions for diagnosing and treating a neurodegenerative disease, the computer instructions comprising instructions for:
  acquiring magnetic resonance spectroscopy data from brain tissues of a subject, by using a data acquisition technique that suppresses resonances in a spectrum, to improve quantification accuracy for metabolites of interest, wherein the data acquisition technique is PRESS-J; and quantifying a metabolite concentration or a metabolite concentration ratio for at least N-acetyl aspartate and/or and N-acetyl aspartate/Creatine from the spectral data as an indicator of a neurodegenerative disease.

23. The memory circuit of claim 22, further comprising computer instructions for monitoring a change in the metabolite concentration or the metabolite concentration ratio for N-acetyl aspartate and/or and N-acetyl aspartate/Creatine over time.

* * * * *